United States Patent [19]
Mori et al.

[11] Patent Number: 6,141,582
[45] Date of Patent: Oct. 31, 2000

[54] IONTOPHORESIS SYSTEM AND ITS CONTROL PROCESS OF CURRENT

[75] Inventors: Kenji Mori; Katsuhiro Nakamura; Naruhito Higo; Noriyuki Kuzumaki, all of Ibaragi-ken, Japan

[73] Assignee: Hisamitsu Pharmaceutical Co., Ltd., Saga-ken, Japan

[21] Appl. No.: 09/000,163

[22] PCT Filed: Aug. 12, 1996

[86] PCT No.: PCT/JP96/02286

§ 371 Date: May 5, 1998

§ 102(e) Date: May 5, 1998

[87] PCT Pub. No.: WO97/07853

PCT Pub. Date: Mar. 6, 1997

[30] Foreign Application Priority Data

Aug. 31, 1995 [JP] Japan .................................. 7-248460
Oct. 17, 1995 [JP] Japan .................................. 7-294837

[51] Int. Cl.[7] ........................................ A61N 1/30
[52] U.S. Cl. ................................. 604/20; 604/501
[58] Field of Search .......................... 604/20–21, 501, 604/503; 607/149, 153, 62

[56] References Cited

U.S. PATENT DOCUMENTS 4,764,164  8/1988  Sasaki .
5,499,967  3/1996  Teillaud et al. .
5,697,896  12/1997  McNichols et al. .

FOREIGN PATENT DOCUMENTS 63-102768  5/1988  Japan .
63-502404  9/1988  Japan .
2-45461   10/1990  Japan .
3-49589    7/1991  Japan .
4-1634     1/1992  Japan .
95/00200   1/1995  WIPO .

*Primary Examiner*—Mark Bockelman
*Attorney, Agent, or Firm*—Sughrue, Mion, Zinn, Macpeak & Seas, PLLC

[57] ABSTRACT

An iontophoresis system and its control process for current are proposed, which system can decrease variation in drug delivery quantity due to the individual difference of impedance of skin or mucosal membrane, and avoid any decrease of the delivery quantity of drug in a donor device, thereby to obtain excellent medicinal effect, safety, reliability, and productivity, comprising said donor device, a reference device, a current detection unit for measuring as an effective current value the difference between the value of an applied current passing between the donor and reference devices during application of pulse voltage/current and the value of a discharged current whose electric charge which the living body has been equipped with is released by a short-circuit formed between said donor and reference devices when the application of pulse voltage/current is suspended, and a feedback control unit of making the amplitude of the pulse voltage/current variable to control the effective current value. The control process for current of the iontophoresis system of the present invention comprises an effective current measurement step of measuring said effective current value and a feedback control step of controlling said effective current value.

10 Claims, 9 Drawing Sheets

1. a power source member
2. a set up circuit member
3. a reference voltage generating member
4. a voltage control member
5. an oscillating circuit member
6. an output circuit member
7. a depolarization circuit member
8. a current detection member
9. a voltage conversion circuit member
10. a display member
11. an output terminal
12. an output terminal 1. a power source member
2. a set up circuit member
3. a reference voltage generating member
4. a voltage control member
5. an oscillating circuit member
6. an output circuit member
7. a depolarization circuit member
8. a current detection member
9. a voltage conversion circuit member
10. a display member
11. an output terminal
12. an output terminal

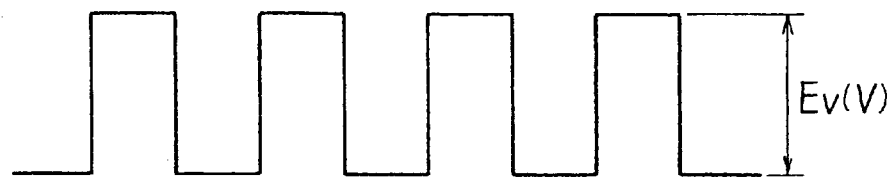
Fig. 6 (b)
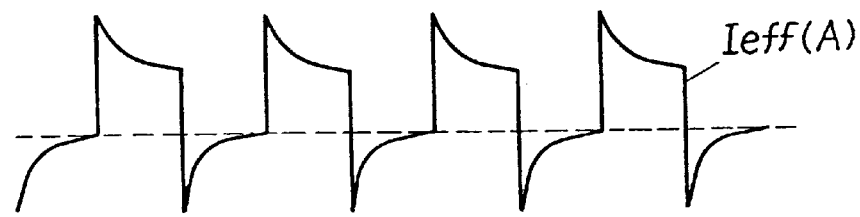
Fig. 6 (c)
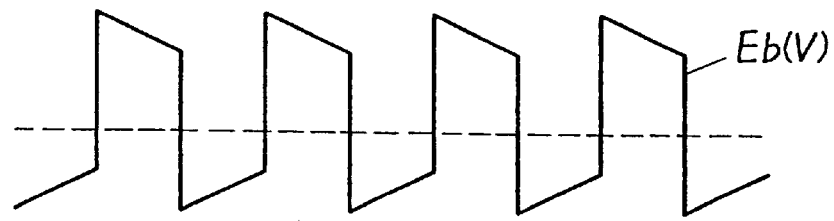
Fig. 6 (d)
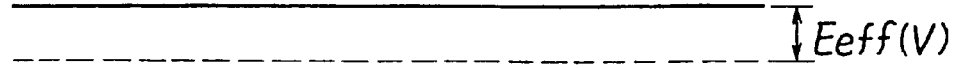

IONTOPHORESIS SYSTEM AND ITS CONTROL PROCESS OF CURRENT

This application is a 371 of PCT/JP96/02286 filed on Aug. 12, 1996.

FIELD OF ART

The present invention relates to an iontophoresis system for introducing a drug into the living body by putting electrodes provided with the drug in contact with skin or mucosal membrane to apply electric current between the electrodes, and its current process for control.

BACKGROUND ART

Studies have recently been performed about the iontophoresis using the electric driving force in order to enhance the absorption of drugs which have been introduced from the skin or mucosal membrane into the living body. The iontophoresis is a process comprising steps of applying a donor device having an electrode including a drug holding layer and a reference device pairing off with said donor device and having an electrode free from drug to the skin or mucosal membrane, and applying an electric current across the both electrodes, one of them forming an anode or another an cathode, so as to promote absorption of the drugs into the living body.

In contrast to the oral administration known as a general drug administration method, the iontophoresis is characterized in that it may be easy to administer a drug, maintain the concentration of the drug in the blood, and avoid any side effect of the drug on the digestive organs, and the iontophoresis system provided with the donor device, reference device, and a current-carrying device for energizing these devices have been studied eagerly and developed.

The relationship between the value of a supplied electric current and a dose at the time when a drug administration takes place using the conventional iontophoresis system will now be described with reference to FIG. 12.

FIG. 12 shows an equivalent circuit of identifying the skin electrically, where R1 designates an ohmic resistance, R2 a polarization resistance, and C a polarization capacity.

When a direct current or voltage/current having pulse wave-forms is applied between the donor and reference devices so as to energize the skin, the electric current will be allowed to pass through the ohmic resistance R1 and polarization resistance R2, and at the same time, an electric charge will be accumulated in the polarization capacity C. And then, if the electric charge of a predetermined quantity of electricity is accumulated in the polarization capacity C, most of the electric currents will pass through the ohmic resistance R1, and then, an electric current having a value substantially equal to that of the current as applied between the donor and reference devices will pass through the skin. At this time, since the current value present in the skin and the quantity of drug delivered to the skin (thereafter referred to as "drug delivery quantity") are directly proportional to each other, the drug delivery quantity can be predicted to some degree based on said electric value.

However, with the process for applying direct current or pulse wave form voltage/current, a complete charging of the polarization capacity C may cause the whole electric currents to concentrate on the ohmic resistance R1 so as to give an electric stimulus to the skin or mucosal membrane, whereby any supplied current value can not be raised to a higher level, with the consequential restriction laying down on the dose.

It would be possible that in the application of pulse wave-form voltage/current, electric charges as accumulated in the polarization capacity C during the suspension of voltage/current application are fully discharged with an exceedingly reduced ratio of the time for which the application of voltage/current is carried out for one pulse (thereafter referred to as pulse duty ratio); such a method will prolong the period of time required for drug administration, such that there had arisen a problem that the drugs applied may not work effectively.

In this connection, a variety of studies have been performed about the power supply, donor device, and reference device as well as the current-carrying method in order to reduce as much as possible electric stimulus which may be given to the skin or mucosal membrane, and to administer drugs efficiently and smoothly.

For example, published Japanese patent applications Nos.2-45461, 3-49589, and 4-1634 disclosed pulse depolarization-type current-carrying method as a current-carrying method in which electric charges which the polarization capacity C has been equipped with may be discharged actively. Such methods arrange within a current-carrying device a circuit forming a short-circuit between the donor and reference devices in such a manner that electric charges as accumulated in the polarization capacity C during a suspension of pulse application being made as per each pulse will be actively discharged (depolarized). Since such a depolarization may reset the equivalent circuit as shown in FIG. 12 into the state where no electric charge is stored within the polarization capacity C, in the next application of pulse waves, an electric current will pass through the ohmic resistance R1, polarization resistance R2, and polarization capacity C as well, thereby to lead to the decrease of chance of electric stimulus being given to the skin or mucosal membrane.

Then, a detection method for current value for determining the drug delivery quantity in a conventional pulse depolarization-type iontophoresis system will be described.

FIG. 13 is a view for the detection of current for use in a conventional constant current controlled pulse depolarization-type iontophoresis system.

Referring to FIG. 13, A1 and A2 identify an ammeter of measuring a current passing through the living body, and SW a switch for performing the pulse depolarization. As shown by this drawing, in this conventional pulse depolarization-type iontophoresis system, the ammeter is placed in the position labeled as A1 or A2 to measure electric current which passes through the living body at the time of application of pulse. That is, the value of current is a total of the value of a current (thereafter referred to as "load current value") passing through the ohmic resistance R1 and polarization resistance R2, and the current value of electric charges stored in the polarization capacity C, said total being identical to a current value to be applied (thereafter referred to as "applied current value"). Thus, the control of drug delivery quantity is achieved by the control of a current quantity passing through the living body in view of the applied current value which has been measured in the event of current.

Next, the structure of the donor device for use with the conventional iontophoresis system will be described.

FIG. 14 is a sectional view showing the components of a conventional donor device. In this drawing, 41 designates a donor device, 42 an electrode, 17 a drug holding layer, and 18 a lead wire.

As shown in FIG. 14, the conventional donor device 41 comprises the electrode 42 which affords a dynamic support to the drug holding layer 17 as well as applies to the drug holding layer 17 a voltage or current, the drug holding layer 17 formed by the drug holding member impregnated with a drug for supplying by means of a voltage or a current applied via an electrode 42 the drug to the skin or mucosal membrane abutted on the lower end face, and the lead wires 18 made of copper, gold, platina, sliver, etc., for supplying to the electrode 42 an electric current from the current-carrying device.

The electrode 42 is roughly divided into a polarizable electrode of generating polarization therewithin at the application of voltage, as is often the case with platina, gold, carbon, titan etc., and an unpolarizable electrode where no polarization occurs at the application of voltage, like silver, silver chloride, copper, copper chloride etc.

The polarizable electrode is low in energy efficiency because the voltage drop due to the polarization acts to lower the substantial voltage for transmission or delivery of drugs. In addition, the polarization tends to bring about a change of pH of solution in the drug holding layer adjacent to the electrode to such an extent that the drug may change its nature, thereby to cause a reduction in the medicinal effectiveness or a stimulus given to the skin. In the view of such problems, there is a trend toward frequent application of the unpolarizable electrode.

On the other hand, the following studies are also taking place about the donor device using the unpolarizable electrode in order that drugs may be introduced into the living body more effectively.

For example, Japanese Patent Laid-Open No.63-102768 (thereafter referred to as "publication A") disclosed "a donor device including a moisture restoring layer interposed between an electrode and a drug-containing layer and a sealing cover provided outside the electrode", reciting that a sufficient restoring of moisture in the drug-containing layer during the current passing will enable an effective percutaneous absorption.

Additionally, Japanese Patent Laid-Open No.63-502404 (thereafter referred to as "publication B") disclosed "a donor device having a first storing member for containing electrolytes, a second-storing member adjacent to said first storing member for containing effective components, and an ion exchange membrane serving as a preventive member against ion emigration for preventing any possible pass between the first and second storing members of ions having an electric charge equivalent to that of at least partially ionized components", with a description that such an arrangement can improve the rate and efficiency at which drugs may be delivered to the affected site, and that prevention may be possible of skin traumas including a chemical burn caused by uncontrollable production between the donor and reference devices of protons or hydroxide ions, and an electric burn caused by the use of a high electric current.

Furthermore, WO No.95/00200 (thereafter referred to as "publication C") disclosed a donor device containing a conductive solution between a reversible electrode and a drug holding means, indicating that avoidance can be made of any decrease in the transport number of ionized drugs due to various kinds of ions which have been liberated from the reversible electrode during the current passing, and that the delivery efficiency of ionized drugs into the body may be improved.

Above-mentioned conventional iontophoresis system and the current-supplying method therefor, however, had the following problems.

1) The ohmic resistance R1, polarization resistance R2, and polarization capacity C in the equivalent circuit as shown in FIG. 12 vary in their values with individuals to be furnished with a drug, and it is difficult to accurately estimate the drug delivery quantity from an applied current value on the grounds that even though using the same takes place with one and the same applied current values, the current value substantially involved in the drug administration may change according to each individual. Consequently, even in the case of the same applied current value used, there may occur variation in the delivered quantity of a drug that is absorbed into the respective individual, which may give rise to a loss of reliability.

2) If the iontophoretic treatment is conducted at regular intervals, eventual accumulation of the variations in the drug delivery quantity as recited in the article 1 is likely to make a difference between the drug delivery quantity and therapeutic effect, which is problematic in that the therapeutic reliability may be lost.

3) Administration of a drug having its therapeutic range and toxic range of the concentration thereof in blood which stand close to each other (a narrow therapeutic window) must be carried out with the greatest care because there is no correct grasping of the drug delivery quantity as indicated in the article 1, and moreover, in some cases, it is inevitable that the dose can not help but be restricted.

4) When the unpolarizable electrode is used in the donor device, ions that have eluted from the unpolarizable electrode to the drug holding layer during the current passing hinder the transfer of a drug so as to lower its transport number, and decrease the drug movement amount toward the target site, thus resulting in reduction of medicinal efficiency.

5) There lies a problem in publication A that since ions eluted from the unpolarizable electrode diffuse within the moisture restoring layer before they reach the drug-containing layer, there may be a reduction of medicinal effect as in the article 4.

6) There lies a problem in publications B and C that though the ion exchange membrane acts to prevent ions eluted out of the electrode from traveling to the layer for containing drugs, the electrolytes contained in the first storing member and the conductive solution adversely affect the absorption of drugs into the skin in such a fashion that the required medicinal effect can not sufficiently be achieved.

The present invention is, for the solution of the above mentioned conventional tasks, to provide an iontophoresis system which is simple in structure, and excellent in medicinal effect, safety, reliability, and productivity, wherein variation in the drug delivery quantity due to the individual differences in the impedance of skin and mucosal membrane may be decreased, the reduction of drug delivery quantity due to the elution of ions from the unpolarizable electrode in the donor device may be avoided, and a constant quantity of drugs may be smoothly delivered into the living body with high efficiencies of delivery and energy; and a control process for current of an iontophoresis system having an excellent medicinal effect, wherein the influence of the individual difference in the impedance of skin or mucosal membrane may be decreased to smoothly deliver a constant quantity of physiologically activated substances into the living body.

DISCLOSURE OF THE INVENTION

For the purpose of solution of said tasks, the iontophoresis system in accordance with the present invention is a pulse depolarization-type iontophoresis system comprising a donor device and a reference device so as to apply pulse voltage/current into the living body interposed between the donor and reference devices; a current detection unit for measuring the difference as an effective current value between the value of an applied current passing between the donor and reference devices during the application of pulse voltage/current, and the value of a discharged current whose electric charge which the living body has been equipped with is discharged by a short-circuit formed between the donor and reference devices when the application of pulse voltage/current is suspended; and a feedback control unit of controlling the effective current value by making the amplitude of the pulse voltage/current variable.

The above-mentioned arrangement may provide an iontophoresis system which is simple in structure, and excellent in medicinal effect, safety, reliability, and productivity, wherein variation in the drug delivery quantity due to the individual difference in the impedance of skin and mucosal membrane may be decreased, the reduction of drug delivery quantity due to the elution of ions from the unpolarizable electrode in the donor device may be avoided, and a constant quantity of drugs may be smoothly delivered into the living body with high efficiencies of delivery and energy.

The control process for current of the iontophoresis system in accordance with the present invention is a control process for current of a pulse depolarization-type iontophoresis system comprising a donor device and a reference device so as to apply pulse voltage/current into the living body interposed between the donor and reference devices, wherein the process comprises an effective current measuring step of measuring as an effective current value the difference between the value of an applied current passing between the donor and reference devices during the application of pulse voltage/current and the value of a discharged current whose electric charge which the living body has been equipped with is discharged by a short-circuit formed between the donor and reference devices when the application of pulse voltage/current is suspended, and a feedback control step of controlling the effective current value by making the amplitude of pulse voltage/current variable.

The above-mentioned arrangement may provide a control process for current of the iontophoresis system having an excellent medicinal effect, wherein the influence of the individual difference in the impedance of skin or mucosal membrane may be decreased so as to smoothly deliver a constant quantity of physiologically activated substances into the living body.

The invention as defined in claim 1 relates to a pulse depolarization-type iontophoresis system comprising a donor and reference devices so as to apply pulse voltage/current into the living body interposed between the donor and reference devices; a current detection unit for measuring as an effective current value the difference between the value of an applied current passing between the donor and reference devices during the application of pulse voltage/current and the value of a discharged current whose electric charge which the living body has been equipped with is discharged by a short-circuit formed between the donor and reference devices when the application of pulse voltage/current is suspended; and a feedback control unit of controlling the effective current value by making the amplitude of the pulse voltage/current variable.

The above-mentioned arrangement enables the most appropriate grasping of a current value substantially involved in the introduction of drugs to the skin or mucosal membrane as an effective current value of the values of applied current as supplied between the donor and reference devices, changing of a pulse voltage/current applied between the donor and reference devices by means of the feedback control unit for the control of this particular effective value of current, thereby to decrease the variation of the drug delivery quantity due to the individual differences in the impedance of skin and mucosal membrane, and smooth delivering of a constant quantity of drugs into the living body.

Further actions make it possible to accurately control and maintain the actual drug delivery quantity by controlling the effective current value with reference to the predetermined drug delivery quantity, so that it is possible to administer a drug safely and effectively to such an extent that the medicinal effect may be considerably improved.

The fact that the drug delivery quantity can be correctly grasped enables the administrations of highly safe and reliable drugs, inclusive of the administration of drugs where the therapeutic range and toxic range of the concentration thereof in the blood stand close to each other (a narrow therapeutic window).

Here, the effective current value Ie is defined as a difference between the absolute value of an applied current value Im passing through the living body interposed between the donor and reference devices at the time of application of pulse voltage/current and the absolute value of a value Id of discharged current whose electric charge with which the polarization capacity C of the living body is discharged between the donor and reference devices when the application of pulse voltage/current is suspended (Ie=|Im|−|Id|).

The applied current value during the application of pulse voltage/current is a total amount of the value of a current with which the polarization capacity C in the living body is electrically charged and the value of a current passing through the ohmic resistance R1 and polarization resistance R2, and includes an electric current which is destined to electrically charge the polarization capacity C, whereby this specific value may not be an effective current value which is substantially involved in the introduction of drugs into the living body. Therefore, in accordance with the present invention, the effective current value Ie, which is a value as resulted from the deduction of the current value with which this polarization capacity C is electrically charged from the applied current Im, is so controlled as to decrease any variation of the drug delivery quantity which may occur due to the individual differences in the impedance of skin and mucosal membrane to ensure that the drug delivery quantity will be determined with a considerable degree of accuracy.

Use is made, as the value of a current with which the polarization capacity C is electrically charged, of the discharged current value Id at the time when an electric charge with which the polarization capacity C within the living body has been charged by a short-circuit formed between the donor and reference devices when the application of pulse voltage/current is suspended because if the donor and reference devices are short-circuited, electric charges as accumulated within the polarization capacity C will be discharged through the ohmic resistance R1 and polarization resistance R2 as well as the short-circuit, but the current passing through the ohmic resistance R1 and polarization resistance R2 is very small, the current value with which the polarization capacity C is substantially charged and the discharged current value Id are identical to each other, and it is easier to measure the electric current passing through the polarization capacity C at the time of electric discharge than that of electric charge.

In accordance with the invention of claim 2 as defined in claim 1, the current detection unit acts to convert the effective current value into the effective voltage value, and the feedback control unit exerts a feedback control on the amplitude of the pulse voltage/current.

The said arrangement enables voltage comparison by the use of a generated reference voltage, which may make the circuit structure very simple in such a manner that the system can be made small in size.

In order to carry out the feedback control, the feedback control unit may convert the effective current as measured in a current detecting circuit member into a voltage, on the basis of the reference voltage established by the use of a voltage from the power supply to get substantially constant the effective current passing through the living body by controlling the amplitude of a voltage/current to be applied into the living body. The reference voltage may be controlled in response to the differences of drugs or individual capacitance or resistance values or symptoms by providing control for making the reference voltage variable by the use of a CPU (Central Processing Unit).

Said power source involves manganese battery, alkali battery, lithium battery, nickel/cadmium battery, silver oxide battery, mercury battery, pneumatic battery, alkali/manganese battery, plastic battery, and button form battery, sheet form battery made of said materials.

In accordance with the invention of claim 3 as defined in claim 2, the current detection unit is provided with a smoothing resistance of smoothing into a substantially constant value the effective voltage value which is a conversion from the effective current value.

Said arrangement enables a stable feedback control with the usual comparison of the effective voltage when a comparator issued, a considerable decrease of an electric stimulus given to the skin or mucosal membrane because of a small local fluctuation of the pulse voltage in amplitude.

In accordance with the invention of claim 4 as defined in any of claims 1 to 3, the feedback control unit exerts a variable control on the period of pulse voltage/current or pulse duty ratio.

Said arrangement enables holding of the measuring accuracy of the effective current within a predetermined limit by optimizing the time for which the polarization capacity C is electrically charged during the current passing and the time for which the electric charge accumulated in the polarization capacity C is discharged dependent on the magnitude of the polarization capacity C in the living body, so that the drug delivery quantity may be measured accurately to control the drug delivery quantity promptly.

In accordance with the invention of claim 5 as defined in any of claims 1 to 4, a depolarization circuit member which may short-circuit the donor and reference devices through a resistance at the suspended application of pulse voltage/current is arranged between the donor and reference devices.

Said arrangement enables conversion of an electric current passing through the resistance to a voltage, and easy formation of the depolarization circuit member with the result that the system can be made small in size.

Here, this particular depolarization circuit may be embodied by a transistor switch such as FET switch and the like.

In accordance with the invention of claim 6 as defined in any of claims 1 to 5, the donor device comprises an unpolarizable electrode, an ion exchange layer, and a purified water layer disposed between the unpolarizable electrode and ion exchange layer, and having a purified water.

Said arrangement enables decrease of voltage loss in the donor device, avoidance through the ion exchange layer of any obstacle to drug movement by ions coming out of the unpolarizable electrode to suppress any possible drop of the transport number of a drug for effective delivery of the drug into the body and accurate control of the drug delivery quantity.

Silver, copper, silver chloride, copper chloride etc., may be used as said unpolarizable electrode.

For said ion exchange layer may be used an ion exchange resin and the like comprising a copolymer made of copolymerizing divinylbenzene and styrene and containing sulfone group or amino group, an anion exchange resin in the event that a drug to be introduced into the living body is positive charged, and a cation exchange resin in case that said drug is negative charged.

Ion exchange water or Japanese Pharmacopoeia purified water may appropriately be used as said purified water in the purified water layer.

In accordance with the invention of claim 7 as defined in claim 6, the purified water layer is provided with a purified water holding member impregnated with purified water.

Said arrangement enables improvement of said purified water layer in mechanical strength, strong joining of said purified water layer, unpolarizable electrode, and ion exchange layer by positioning the unpolarizable electrode and the ion exchange layer at regular intervals, and increasing the contact area, and improvement of the electric conductivity of said purified water layer.

For said purified water holding member may be used unwoven cloth, paper, gauze, absorbent wadding, polyporus layers and foaming agent such as polyethylene having a series of foams, polypropylene, vinyl acetate, polyolefin foam, polyamide foam, polyurethane; natural polysaccharides such as karaya gum, gum tragacanth, xanthangum, starch, gum of arabic, echo gum, locust bean gum; gelatin, pectin, agar, polyvinyl alcohol and its saponifiers, polyvinyl formal, polyvinyl methyl ether and its copolymer; polyvinyl pyrrolidone and its copolymer; polyhema group, and its cross linked members.

The content of purified water in the purified water holding member should preferably be 10 to 3000 w/w %. The content below 10 w/w % is unpreferable because it tends to invite a decrease of electric conductivity. In addition, the content of over 3000 w/w % is also unpreferable because in such a case, a purified water can not be held to cause a leakage, or the distance between the unpolarizable electrode and ion exchange layer might be increased to cause a drop of the electric conductivity.

In accordance with the invention of claim 8 as defined in claim 6 or 7, said purified water layer has a thickness of 0.01 to 4 mm.

Said arrangement makes it easy to form a purified water layer and to control an electric current passing through the purified water layer.

Here, the thickness of the purified water layer should preferably be 0.01 to 3 mm, and more preferably 0.01 to 2 mm. If the purified water layer is under 0.01 mm in thickness, it will be difficult to form a purified water layer to cause a fall of productivity or mass productivity, and if the thickness of the purified water layer comes in over 2 mm, a voltage drop or a reduction in the supplied current value as resulting from the low electrical conductivity of a purified water will occur in the purified water layer so as to cause a tendency toward decrease of the drug delivery efficiency. Either case is, therefore, unpreferable.

In accordance with the invention of claim 9 as defined in any of claims 6 to 8, said purified water has an electrical conductivity of 0.01 to 1500 $\mu\Omega^{-1} \cdot cm^{-1}$.

Said arrangement may effectively prevent any movement of ions eluted from the unpolarizable electrode to the drug holding layer, and improve the delivery efficiency of drug into the living body.

Here, the electric conductivity of purified water should preferably be 0.01 to 1000 $\mu\Omega^{-1} \cdot cm^{-1}$. If the electric conductivity of purified water is lower than 0.01 $\mu\Omega^{-1} \cdot cm^{-1}$, the current value supplied to the drug holding layer will become considerably small to cause a tendency toward difficulty in the delivery of drug into the living body, while as the electric conductivity goes beyond 1000 $\mu\Omega^{-1} \cdot cm^{-1}$, electrolytes contained in the purified water permeate the ion exchange layer so as to cause a tendency toward decrease of the delivery efficiency of drug. Therefore, either case is unpreferable. If the electric conductivity of purified water exceeds 1500 $\mu\Omega^{-1} \cdot cm^{-1}$, the above-mentioned tendency will become more pronounced, which is unpreferable in particular.

The invention as defined in claim 10 is a process of controlling an electric current of the pulse depolarization-type iontophoresis system comprising donor and reference devices to introduce pulse voltage/current into the living body interposed between said donor and reference devices, which process comprising an effective current measurement step of measuring the difference as an effective current value between the value of an applied current passing between the donor and reference devices during application of pulse voltage/current and a discharged current value whose electric charge which the living body is equipped with is discharged by a short-circuit formed between the donor and reference devices when the application of pulse voltage/current is suspended, and a feedback control step of making the amplitude of pulse voltage/current variable to control the effective current value.

Said arrangement enables an accurate control of a predetermined drug delivery quantity to administer drugs safely and effectively, thereby to ensure that the medicinal effect will be substantially improved and that the drug delivery quantity will be maintained up to such a high accuracy.

Examples of drugs for use in said iontophoresis system involves central analgesics such as morphine, fentanyl, pethidine, codeine, buprenorphine, butorphanol, eptazocine, pentazocine; peptide group such as insulin, calcitonin, calcitonin related genetic peptide, vasopressin, desmopressin, protirelin (TRH), adrenocorticotropic hormone (ACTH), luteinizing hormone releasing hormone (LH-RH), growth hormone releasing hormone (GRH), nerve growth factors (NGF) and the other releasing factors, angiotensin, parathyroid hormone (PTH), thyrothopic stimulating hormone (TSH, thyrotropin), follicle stimulating hormone (FSH), luteal hormone (LH), prolactin, serumal gonad stimulating hormone, human chorionic gonadotropin hormone (HCG), growth hormone, somatostatin, somatomedin, glucagon, oxytocin, gastrin, secretin, endorphin, enkephalin, endothelin, cholestokinin, neurotensin, interferon, interleukin, transferrin, erythropoetin, superoxide dismutase (SOD), glanulate colony-stimulating factor (G-CSF), vasoactive intestinal polypeptide (VIP), muramyl dipeptide, corticotropin, urogastrone, h-ANP; tranquilizers such as carbamazepine, chlorpromazine, diazepam, nitrazepam; antimaligancy drug such as bleomycin, adriamycin, 5-fluorouracil, mitomycin; cardiotonic such as digitalis, dioxin, digitoxin; sex hormone such as estradiol, testosterone; and hypotensive agent such as reserpine, clonidine. However, this invention should not be restricted to the above-described.

The effective current value of the iontophoresis system is commonly 0.01 to 10 mA/cm², and 0.05 to 1 mA/cm² should be preferable, and the voltage applied into the living body is generally around 1 to 20V, subject to change according to the contact area between the skin and the donor and reference device, and preferably 3 to 12V. A limiter based on the voltage value may be provided in case high voltage should be applied in order to obtain the predetermined effective current value. This enables an effective introduction of a drug into the living body, while alleviating pain resulted from an electric current passing through the living body.

BRIEF DESCRIPTION OF THE DRAWINGS

FIG. 6(a) is a view showing voltage waveforms at Point A in the circuit diagram (FIG. 5) of the iontophoresis system in accordance with one embodiment of the present invention;

FIG. 6(b) is a view showing current waveforms at Point A;

FIG. 6(c) is a view showing voltage waveforms at Point B;

FIG. 6(d) is a view showing voltage waveforms at Point C;

THE MOST PREFERRED EMBODIMENTS FOR EMBODYING THE INVENTION

Now, the specific examples of the embodiments in accordance with the present invention will be described with reference to the drawings.

Embodiment 1

Figure 1:
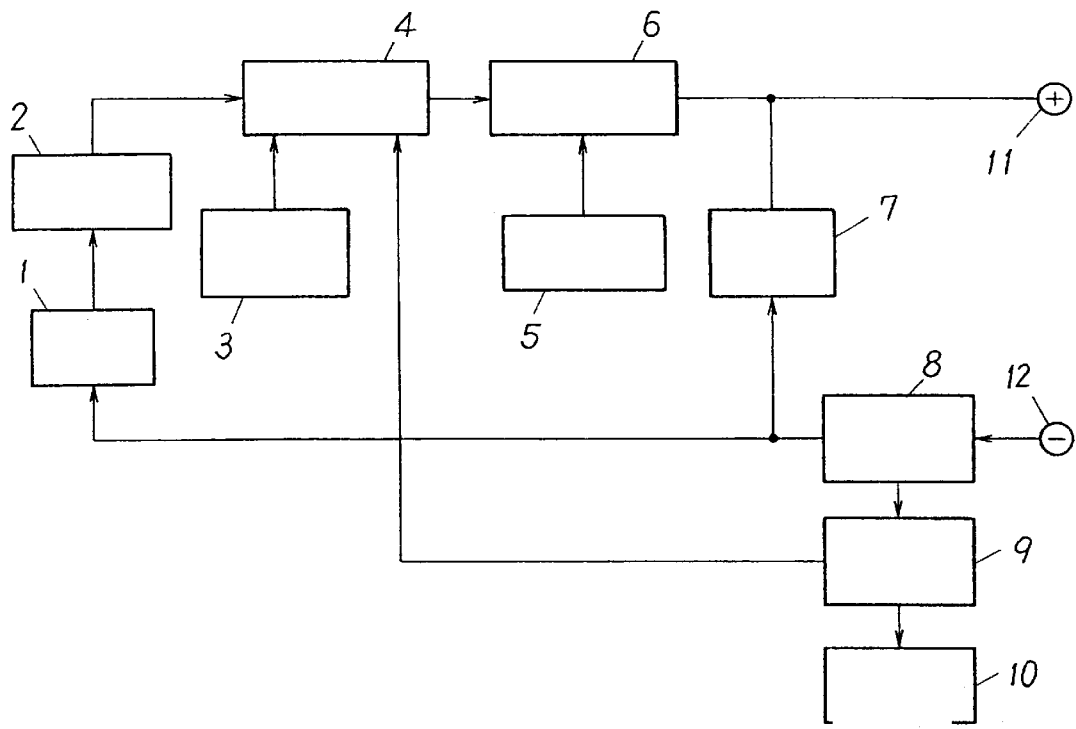
FIG. 1 is a block diagram showing the main components of an iontophoresis system in accordance with one embodiment of the present invention.

FIG. 1 is a block diagram showing the main components of the pulse depolarization-type iontophoresis system in accordance with one embodiment of the present invention.

In the drawing, 1 designates a power source member, 2 a set up circuit member, 3 a reference voltage generating member, 4 a voltage control member, 5 an oscillating circuit member, 6 an output circuit member, 7 a depolarization circuit member, 8 a current detection circuit member, 9 a voltage conversion circuit member, 10 a display member, 11, 12 output terminal.

As shown in FIG. 1, the iontophoresis system embodying the present invention comprises the power source member 1 constituted by a coinform battery for applying pulse voltage/current between a donor device (not shown) and a reference device (not shown), the set up circuit member 2 of increasing a power voltage of the power source member 1 as needed to obtain an output voltage higher than the power voltage of the power source 1, the reference voltage generating member 3 of generating a reference voltage which acts as a standard for comparison with the effective voltage value, the voltage control member 4 of controlling feedback for automatically changing an output voltage value in the output circuit member 6 so that the effective current value will come within the range of 70 to 150% of the predetermined value in comparison of an effective voltage value outputted from the voltage conversion circuit member 9 with a reference voltage established by the reference voltage generating member 3, the oscillating circuit member 5 of pulse modulating to around 1 to 100 kHz of pulse voltage a DC voltage inputted to the output circuit member 6 to set up and alter a pulse frequency or pulse duty ratio of the resultant pulse voltage, the output circuit member 6 of performing switching operations according to the pulse frequency and pulse duty ratio which have been identified by the oscillating circuit member 5 to output as a pulse voltage a voltage value outputted from the voltage control member 4, the depolarization circuit member 7 including a switch portion of switching out the donor device (not shown) and the reference device (not shown) through a resistance when the application of the pulse voltage outputted from the oscillating circuit member 5 is suspended for depolarization of the donor and reference devices (not shown), the current detection circuit member 8 of measuring the values of effective currents allowed to pass through the living body, the voltage conversion circuit member 9 of converting the effective current value as measured in the current detection circuit member 8 to an effective voltage value, the display member 10 of displaying the resulted effective voltage value from the voltage conversion circuit member 9, the output terminal 11 connected with the donor device (not shown) for producing pulse voltage, and the output terminal 12 pairing off with the output terminal 11 and connected with the reference device.

Description will be made of how the iontophoresis system as such arranged as above-mentioned and defining this embodiment will operate.

First, the donor device (not shown) as connected with the output terminal 11 and the reference device (not shown) as connected with the output terminal 12 are attached to a site of human body for drugs to be administered. A drug holding layer is incorporated in the donor device (not shown) on said administration site.

Next, the iontophoresis system is turned on.

Then, a reference voltage of the reference voltage generating member 3 is set up according to situations such as drugs used, patient's symptoms and his or her physical constitution, so as to establish an effective value of current allowed to pass between the donor and reference devices (not shown) accordingly.

Then, pulse frequency, pulse duty ratio of the oscillating circuit member 5, and the duration for pulse to pass are set up, thereafter to start administration of a designed quantity of drug.

The measurement steps for effective current during the drug administration comprises measuring effective current values in the current detection circuit member 8, and converting them to effective values of voltage in the voltage conversion circuit member 9 whenever need arises.

Next, the step for feedback control comprises inputting the resultant effective value of voltage from the voltage conversion circuit member 9 in the voltage control member 4, carrying out a feedback control by means of the voltage control member 4, and keeping the effective current value in a predetermined level for proper maintenance of the administration quantity.

After such drug administration processes, the pulse voltage of the iontophoresis system is automatically cut off, and the donor and reference devices are removed from the administration site, with the consequence that this drug therapy comes to an end.

During said administration, the depolarization circuit member 7 senses any rise/fall of a pulse voltage produced by the oscillating circuit member 5 so as to be turned on/off automatically. At the turn on time of depolarization circuit member 7, there is a short-circuit developed through the resistance between the donor device and reference device, and the electric charges stored in donor device or reference device has been released to make depolarized state.

The position where to measure current in the current detection circuit member 8 of the iontophoresis system in accordance with the present embodiment will be described with reference to FIG. 2.

Figure 2:
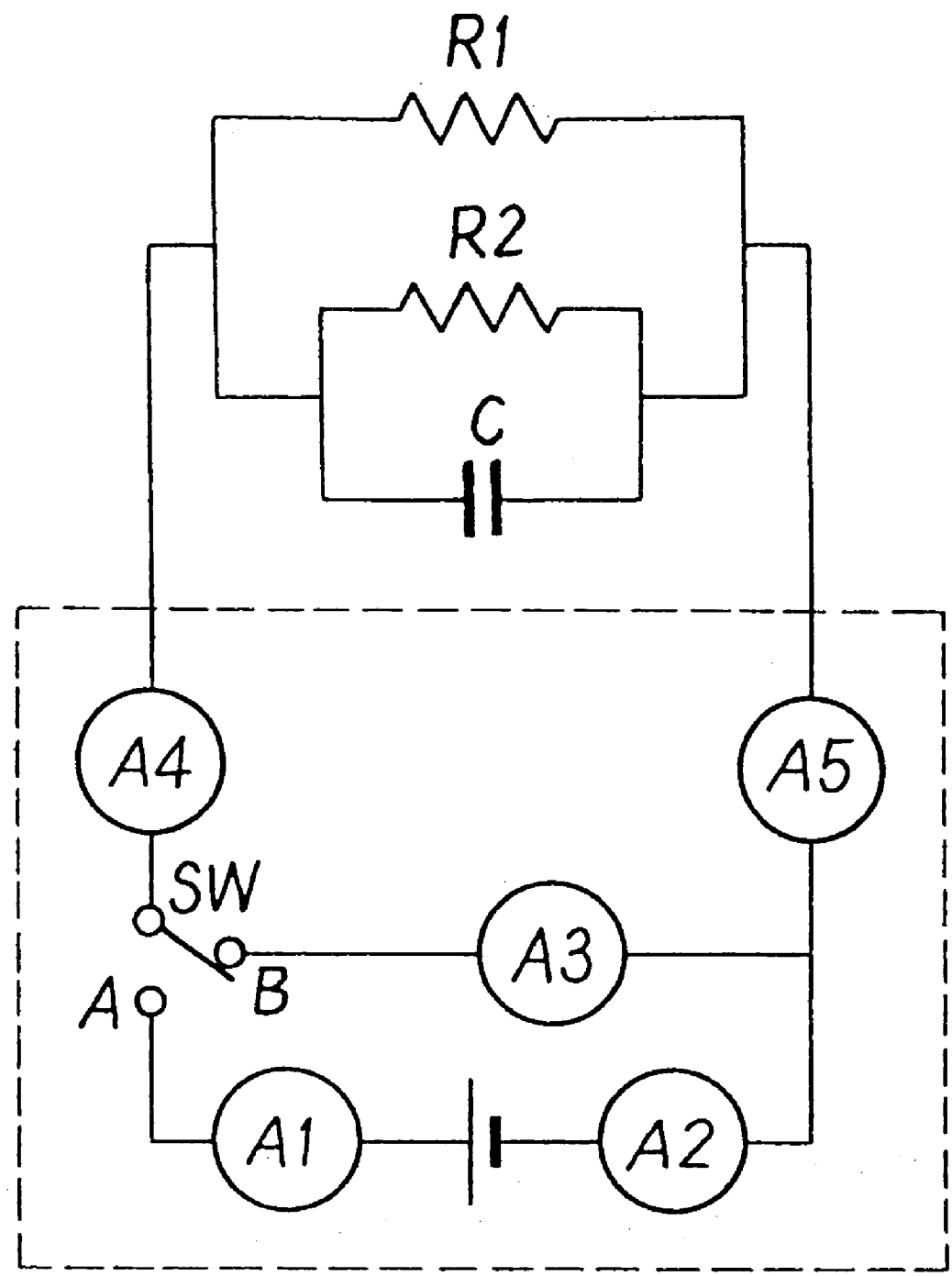
FIG. 2 is a view showing the state of current measurement by a current detection unit of the iontophoresis system in accordance with one embodiment of the present invention.

FIG. 2 is a circuit diagram showing a current measurement position in the current detection circuit of the iontophoresis system in accordance with the present embodiment of the invention.

In the drawing, A1, A2, A3, A4, and A5 identify current detection units, and SW a switch.

Referring to the circuit diagram shown by FIG. 2, the switch SW is coupled to A when a current is allowed to pass, and to B during depolarization. At this stage, current measurements are conducted by the current detection units (A1 and A3) or (A2 and A3) to calculate the effective value of current, or the same process may rely on A4 or A5. In particular, the measurement by the current detection unit A4 or A5 may do with a single current detection unit; this may make the structure of the current detection circuit member so simple that miniaturization of the member can be obtained.

The voltage and current waveforms at the output terminal 11 of the iontophoresis system in accordance with the present embodiment of the invention will be described.

Figure 3:
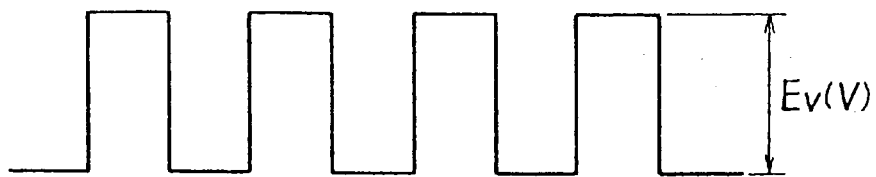
FIG. 3(a) is a view showing an output voltage waveform at an output terminal of the iontophoresis system in accordance with one embodiment of the present invention.
FIG. 3(b) is a view showing a current waveform at an output terminal of the iontophoresis system in accordance with one embodiment of the present invention.
Figure 3:
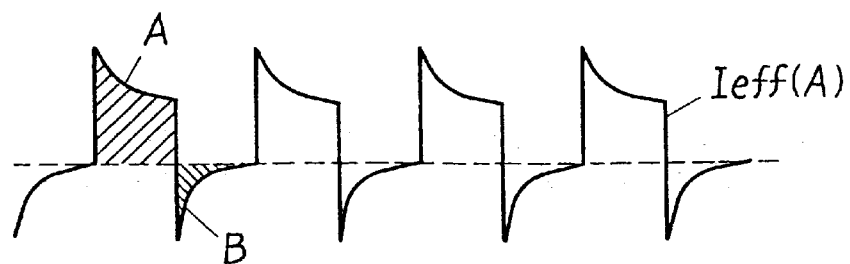

FIG. 3(a) is a view showing a voltage waveform at the output terminal of the iontophoresis system in accordance with one embodiment of the invention, and FIG. 3(b) is a view showing a current waveform at the output terminal of the iontophoresis system in accordance with the one embodiment of this invention.

Referring to FIG. 3(b), the area A indicates the value of an applied current that may pass through the living body when a pulse voltage has been applied, and the area B indicates the value of discharged current when the electric charge accumulated in the polarized capacity C was released during pulse depolarization. This difference between the applied current value at A and the discharged current value at B provides an effective current value.

As discussed above, in accordance with the present embodiment, the values of the applied current allowed to pass between the donor and reference devices, which is substantially involved in the drug administration to the skin or mucosal membrane may be grasped with a great accuracy, and this effective current value is controlled by changing pulse voltage/current applied between the donor and reference devices by means of the feedback control unit so as to decrease variations of the drug delivery quantity which may arise due to differences of individuals in impedance of the skin and mucosal membrane, whereby a constant quantity of drug may be delivered into the living body without difficulty.

A control of the effective current value can keep the actual drug delivery quantity under accurate control and maintenance based on the established drug delivery quantity. This may obtain a safe and effective drug administration for more improvement medicinal effect.

This accurate grasping of drug delivery quantity enables achievement of drug administration with a high safety and reliability inclusive of an administration of drugs having a therapeutic range and toxic range in the concentration thereof in blood standing close to each other (a narrow therapeutic window).

Using an effective voltage resulted from the conversion of effective current value by the current detection circuit member, a feedback control may exert on the amplitude of pulse voltage/current to make the comparison of the voltage with reference voltage, so as to such an extent that the circuit arrangement will be very simple to ensure that the system will be made small in size.

In this embodiment, the control of effective current value is achieved by converting an effective current value as measured by the current detection circuit member to a voltage in voltage conversion circuit member to feed back control the voltage control member for proper control of voltage value transmitted into the living body, but the voltage value, etc. correlated to the effective current value may be fed back to the oscillating circuit member which will make the pulse frequency and pulse duty ratio variable with the current-carrying time kept under control. In this case, the time for charging the polarization capacity C when a current is allowed to pass, and the time for discharging the electric charge accumulated in the polarization capacity C during suspended current application may be optimized according to the magnitude of the polarization capacity C within the living body to retain the measurement accuracy of effective current in the predetermined range, whereby the drug delivery quantity may be precisely measured to such a degree that more improvement of safety and reliability can be obtained and that rapid control of the drug delivery quantity can be acquired.

The oscillating circuit member may be provided with an output limiting circuit for limiting a large peak current passing through the human body at the rise and fall of pulse voltage.

Embodiment 2

Figure 4:
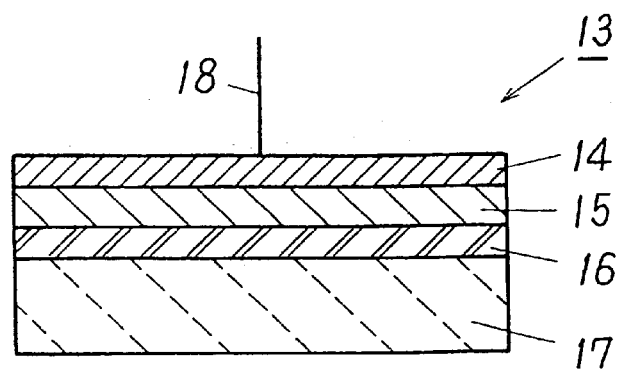
FIG. 4 is a sectional view of the main components of a donor device for use with the iontophoresis system in accordance with one embodiment of the present invention.

FIG. 4 is a sectional view showing the main components of the donor device for use with the iontophoresis system in accordance with the present embodiment of this invention.

In this drawing, 13 indicates a donor device, 14 an unpolarizable electrode, 15 a purified water layer, 16 an ion exchange layer, 17 a drug holding layer, and 18 a lead wire.

As shown by FIG. 4, the donor device 13 in accordance with the present embodiment of this invention comprises unpolarizable electrode 14 free from polarization and having a small voltage drop for applying voltage and supplying current to the drug holding layer 17, purified water layer 15 constituted by a purified water or a purified water holding member impregnated with purified water for dispersing ions eluted from the unpolarizable electrode 14, ion exchange layer 16 constituted by an ion exchange resin adapted to prevent fall in the transport number of drug for separating ions eluted from the unpolarizable electrode 14 from the purified water layer 15 within the purified water, drug holding layer 17 constituted by a drug and a drug holding member for transferring the drug ionized by a voltage applied through the unpolarizable electrode 14 to the skin or mucosal membrane abutted on the lower end face, and lead wire 18 for supplying a current to the unpolarizable electrode 14.

Here, the drug holding member of drug holding layer 17 may be formed by polycarbonate resin, nitrocellulose, nylon resin, polyvinyliden fluoride, polysulfone resin, etc.

The donor device for use with the iontophoresis system in accordance with the present embodiment of this invention will be described with reference to its intended use.

The donor device 13 is abutted with a reference device (not shown) on the skin of a patient to whom a drug is to be given. The lead wire 18 of the donor device 13 and a lead wire of the reference device (not shown) are connected respectively with the output terminals 11 and 12 of the iontophoresis system as shown in FIG. 1 to apply pulse voltage/current there between. This will act to ionize the drug held by the drug holding layer 17. The ionized drug travels along the voltage slope until it infiltrates the skin to be absorbed into the body.

For the reference device, a solution layer containing sodium chloride solution, etc. may be used as an alternative to the purified water layer 15, ion exchange layer 16 and drug holding layer 17.

In accordance with the present embodiment as discussed above, the use of the unpolarizable electrode may reduce voltage loss, and the ion exchange layer may help prevent the drug from being disturbed in its movement by ions eluted from the unpolarizable electrode to restrain a drop of the transport number of the drug in such a manner that the delivery of drug into the body may be executed with a high efficiency and that the drug delivery quantity may be controlled with reasonable accuracy.

The purified water holding member impregnated with purified water may improve the mechanical strength of the purified water layer; the disposition of the unpolarizable electrode and the ion exchange layer made at regular intervals and the enlargement of the contact area contributes to reinforcement of the joining between the purified water layer, unpolarizable electrode and ion exchange layer; and the electric conductivity of the purified water layer may be improved.

The present invention will be described in detail using some examples.

EXAMPLE 1

One example of the pulse depolarization-type iontophoresis system in accordance with the present invention will be described with reference to the drawings.

Figure 5:
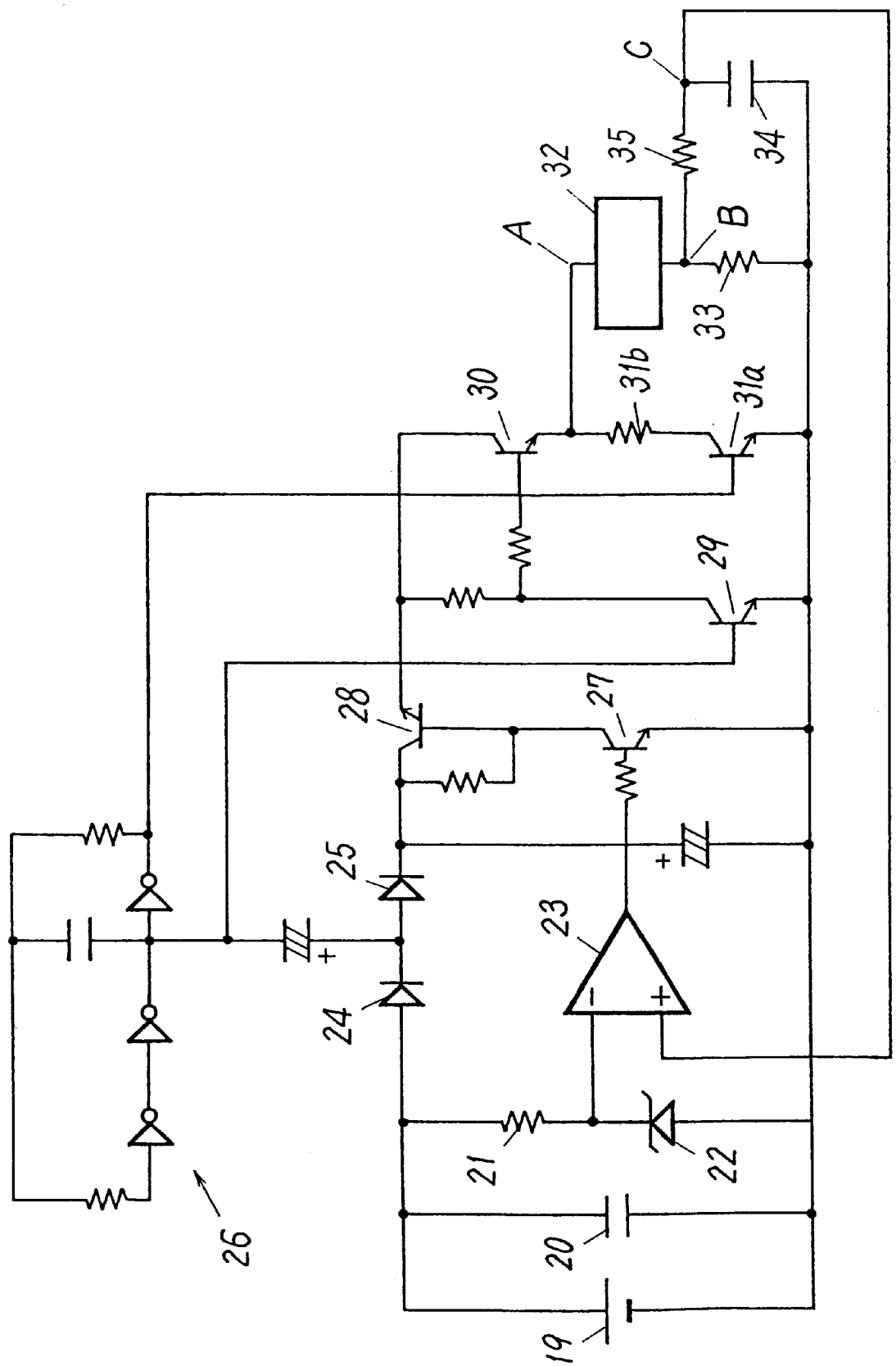
FIG. 5 shows the main circuit of a component of the iontophoresis system in accordance with one example of the present invention.

FIG. 5 is a circuit diagram showing the main components of the iontophoresis system in accordance with the example 1 of this invention. FIG. 5 shows a specific example of the block view of FIG. 1.

In this drawing, 19 designates a battery acting as a power source for circuit, 20 a power source smoothing capacitor, 21 a current limiting resistance, 22 a zener diode, 23 a voltage comparative comparator, 24, 25 voltage doubler producer diodes, 26 an oscillating circuit, 27, 28 output control transistors, 29, 30 pulse output transistors, 31*a* a depolarization transistor, 31*b* a resistance, 32 a load of living body, 33 a current to voltage conversion resistance, 34 an effective current measuring capacitor, and 35 a smoothing resistance.

The iontophoresis system in accordance with the present example as shown in FIG. 5 comprises battery 19 as power source for circuit and power source smoothing capacitor 20 corresponding to the power source 1; current limiting resistance 21 and zener diode 22 corresponding to the reference voltage generating unit 3 for producing a reference voltage; voltage comparative comparator 23 for controlling voltage; voltage doubler producer diodes 24, 25 corresponding to the set up circuit member 2; oscillating circuit 26 consisting of an invertor, a resistance, a capacitor, corresponding to the oscillating circuit member 5, consisting of an invertor, a resistance and a capacitor; output control transistors 27, 28 corresponding to the voltage control member 4 for controlling the amplitude of pulse voltage on the basis of an output voltage from the voltage comparative comparator 23; pulse output transistors 29, 30 corresponding to the output circuit member 6 for converting into a pulse wave a voltage controlled by the output control transistors 27, 28; depolarization transistor 31*a* and resistance 31*b* corresponding to the depolarization circuit member 7; current to voltage conversion resistance 33 corresponding to the current detection unit 8 for measuring effective current value as a voltage; and effective current measurement capacitor 34 wherein the effective current is charged and measured and smoothing resistance 38 for smoothing into a substantially constant value the effective voltage value charged/discharged into the effective current measurement capacitor 34, which correspond to the voltage conversion unit 9.

32 is a load corresponding to the living body to which a drug is to be administered.

With the iontophoresis system, as such arranged as above-mentioned, in accordance with the present example, said effective voltage value as involved in the effective current measurement capacitor 34 is introduced into the voltage-comparative comparator 23, and the effective current value is fed back to the output voltage by taking the comparison with the reference voltage value involved in the zener diode 22 and the effective voltage value involved in the effective current measurement capacitor 34 so as to fix the effective current value on a substantially constant level.

Next, description will be made of the voltage/current wave-forms as observed by the pulse depolarization-type iontophoresis system in accordance with this embodiment.

FIG. 6(*a*) shows a voltage waveform at Point A as shown in the circuit diagram of the pulse depolarization-type iontophoresis system in accordance with the first embodiment of FIG. 5, FIG. 6(*b*) shows a current waveform at Point A of FIG. 5, FIG. 6(*c*) shows a voltage waveform at Point B of FIG. 5, and FIG. 6(*d*) shows a voltage waveform at Point C of FIG. 5.

Referring to the voltage waveform at Point C, the effective voltage value may be measured by the smoothing resistance in a substantially regular form.

As stipulated as above, in this embodiment, the smoothing resistance provided in the current detection circuit for smoothing into a substantial regular value an effective voltage value which is a conversion from the effective current value is capable of performing a stable feedback control in normal comparison with the effective voltage value, which will render smaller the amplitude of pulse voltage in its local fluctuations so as to appreciatively decrease the electric stimulus against the skin or mucosal membrane.

Furthermore, the provision of the depolarization circuit member adapted to form a short-circuit between the donor and reference devices through a resistance when the application of pulse voltage/current is suspended enables conversion of a current passing through the resistance into a voltage. This may, therefore, facilitate the construction of circuits for proper miniaturization of device and remove a polarized potential set up within the living body such as skin and the like when application of pulse voltage/current is suspended, so that electric stimulus against the skin or mucosal membrane may be sufficiently decreased to obtain an effective administration of drugs.

TEST EXAMPLE 1

Concerning the pulse depolarization-type iontophoresis system in accordance with the first example and a conventional pulse depolarization-type and constant current controllable iontophoresis system (a first comparative example), by the iontophoretic administration of calcitonin, a comparative test was made to determine the concentration of calcitonin in the serum.

Referring to the iontophoresis system as used in the first embodiment and the first comparative example, use was made of a donor device constituted by an ion exchange layer produced by steps of placing on a silver electrode with an electrode area of 2.5 cm$^2$ a piece of purified water layer made from an unwoven cloth (WP2085, Japan Vilene) having a thickness of 0.5 mm and an area of 2.5 cm$^2$ and impregnated with 100 μl of purified water (electric conductivity: 0.05 $\mu\Omega^{-1}\cdot cm^{-1}$) and piling on said purified water layer an anion exchange membrane having an area of 3.46 cm$^2$ (A-201, Asahi Kasei), placing on said ion exchange layer a drug holding member of an area of 3.46 cm$^2$ impregnated with 80 μl of purified water (biodyne+, Pole), and dripping salmon calcitonin 250IU on said drug holding member until a drug holding layer was produced. Use was made of a reference device including a silver/silver chloride electrode and polyvinyl alcohol containing salt.

In the iontophoresis system used for the first example, the donor devices were applied to the oral mucosal membranes of three beagles (weight: about 10 kg per each) anesthetized by pentobarbital sodium, the reference devices were secured to their ears, and the both devices were energized for 2 hours by a regular current of 0.7 mA (effective current value).

In the iontophoresis system used for the first comparative example, the donor devices were applied to the oral mucosal membranes of three beagles (weight: about 10 kg per each) anesthetized by pentobarbital sodium, the reference devices were secured to their ears, and the both devices were energized for 2 hours by a constant current 1.5 mA.

In either system, blood was collected for 30 minutes during the current application, and over time for 3 hours after the termination of energization, and the concentration of salmon calcitonin in the serum was measured by the use of a commercial radio immunoassay kit. The result will be described with reference to FIGS. 7 and 8.

Figure 7:
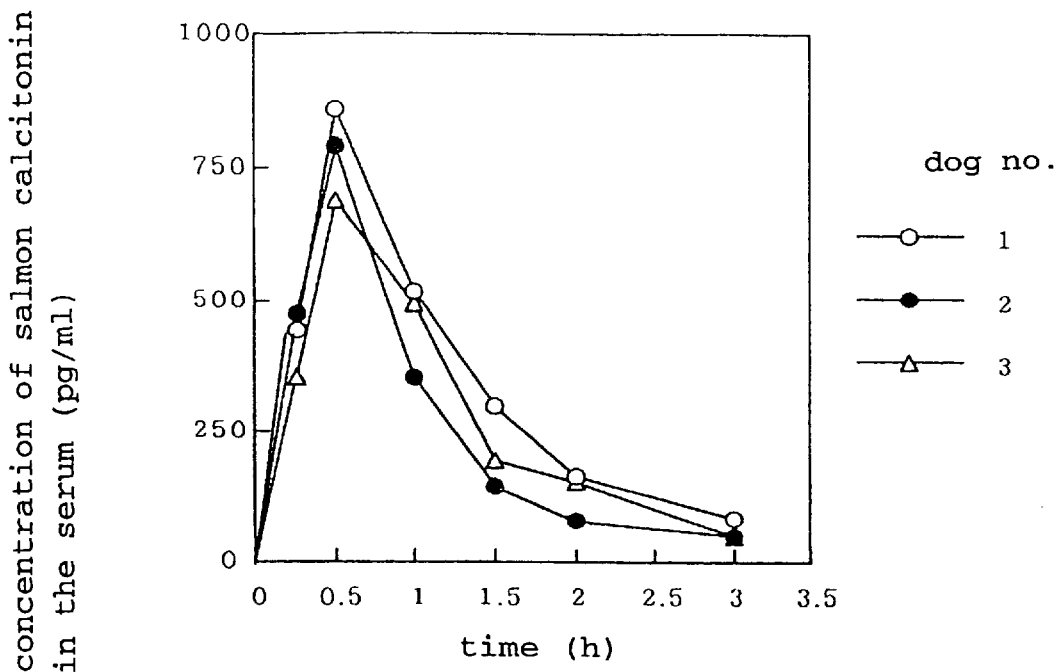
FIG. 7 is a view showing the relation between the current carrying time and the concentrations of salmon calcitonin in the serum of dogs, as observed by the iontophoresis system in accordance with a first example.
Figure 8:
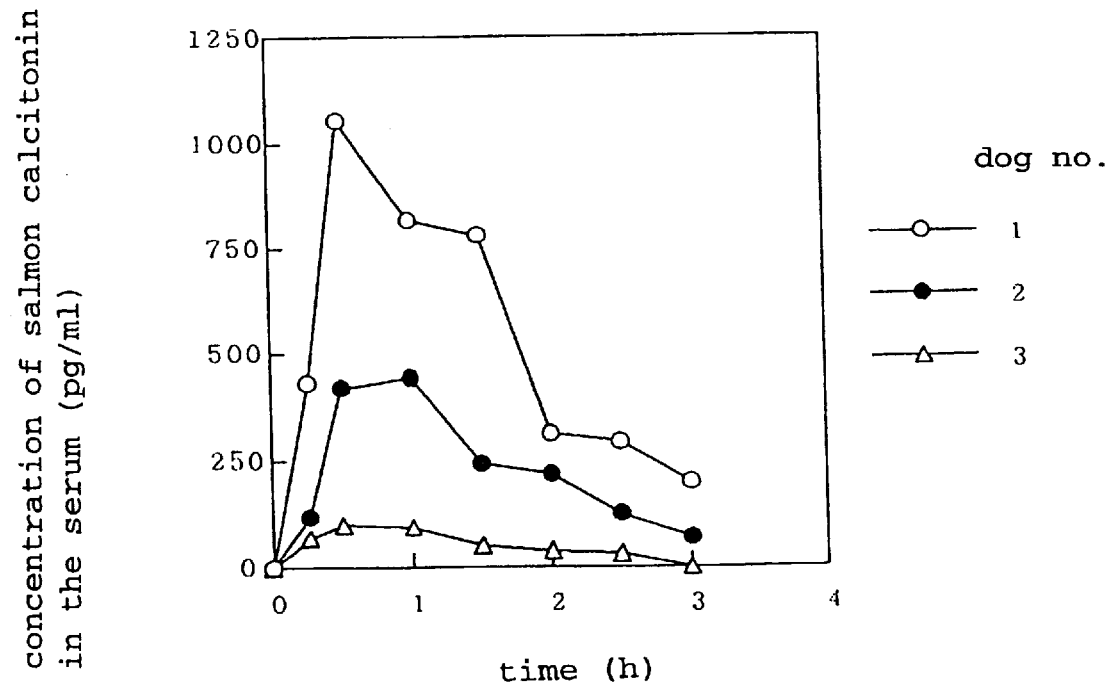
FIG. 8 is a view showing the relation between the current carrying time and the concentrations of salmon calcitonin in the serum of dogs, as observed by the iontophoresis system in accordance with a first comparative example.

FIG. 7 illustrates the relation between the current carrying time and the concentrations of salmon calcitonin in the serums of said dogs as obtained by the use of the iontophoresis system in the first example, and FIG. 8 illustrates the relation between the current carrying time and the concentrations of salmon calcitonin in the serums of said dogs as obtained by the use of the iontophoresis system in the first comparative example.

As apparent from FIG. 7, with the iontophoresis system in accordance with the first example, the maximum concentration of salmon calcitonin in the serum of one of the dogs was 860 pg/ml, and the minimum concentration in another dog was 691 pg/ml; the ratio was 1.2, showing that the individual difference was very small. Additionally, the individual difference in the concentration of salmon calcitonin in the serum after the termination of energization was also found very small as showing FIG. 7.

On the other hand, in the case of the application of a constant current by using the iontophoresis system in accordance with the first comparative example, as shown in FIG. 8, the maximum concentration of salmon calcitonin in the serum was 1059 pg/ml, and the minimum concentration was 95 pg/ml; there has been found a very big difference of more than ten times occurring between the 2 extremes.

The result as discussed above shows that as compared with the conventional constant current controllable pulse depolarization-type iontophoresis system, the pulse depolarization-type iontophoresis system in accordance with the present example is much more advantageous in reducing the individual difference in the drug absorption.

EXAMPLE 2 AND COMPARATIVE EXAMPLES 2, 3

The ion exchange layer is produced by a process comprising steps of placing on a silver electrode of an area of 2.5 cm$^2$ a piece of purified water layer made from an unwoven cloth (WP2085, Japan Vilene) impregnated with 100 µl of purified water (electric conductivity: 0.05 $\mu\Omega^{-1}\cdot cm^{-1}$) and having a thickness of 0.5 mm and an area of 2.5 cm$^2$, and piling on said purified water layer an ion exchange membrane (A-201, Asahi Kasei) having an area of 3.46 cm$^2$. And then, a drug holding member (biodyne+, Pole) impregnated with 80 µl of purified water and having an area of 3.46 cm$^2$ is placed on said ion exchange layer, and salmon calcitonin 201U was dripped on said drug holding member for a complete donor device as shown in the second embodiment has been made for the example 2.

Next was produced for the comparative example 2 another donor device having the same structure as the example 2, but using by way of exception an unwoven cloth (W2085, Japan Vilene) impregnated with 100 µl of saline (electric conductivity: 1500 $\mu\Omega^{-1}\cdot cm^{-1}$) and having a thickness of 0.5 mm and an area of 2.5 cm$^2$.

Further donor device as comparative example 3 was prepared of the same structure as that of example 2, with the exception that it is formed without ion exchange layer.

In addition to these three sorts of donor devices was prepared a reference device made of silver chloride with 12% polyvinyl alcohol gel containing sodium chloride (UF-250G, Unitika) applied thereon.

Any of said three donor devices and said reference device were mounted on the abdomen of a SD rat (weight: about 250 g) to apply a 12 volt pulse depolarization across the electrodes, namely the donor device as an anode, and the reference device as a cathode. In the meantime, blood was collected over time from the rat's jugular vein, followed by a measurement of the concentration of salmon calcinin in the serum being made using a radio immunoassay kit (quantitative kit for peninsula salmon calcitonin). The result will be described with reference to FIG. 9.

Figure 9:
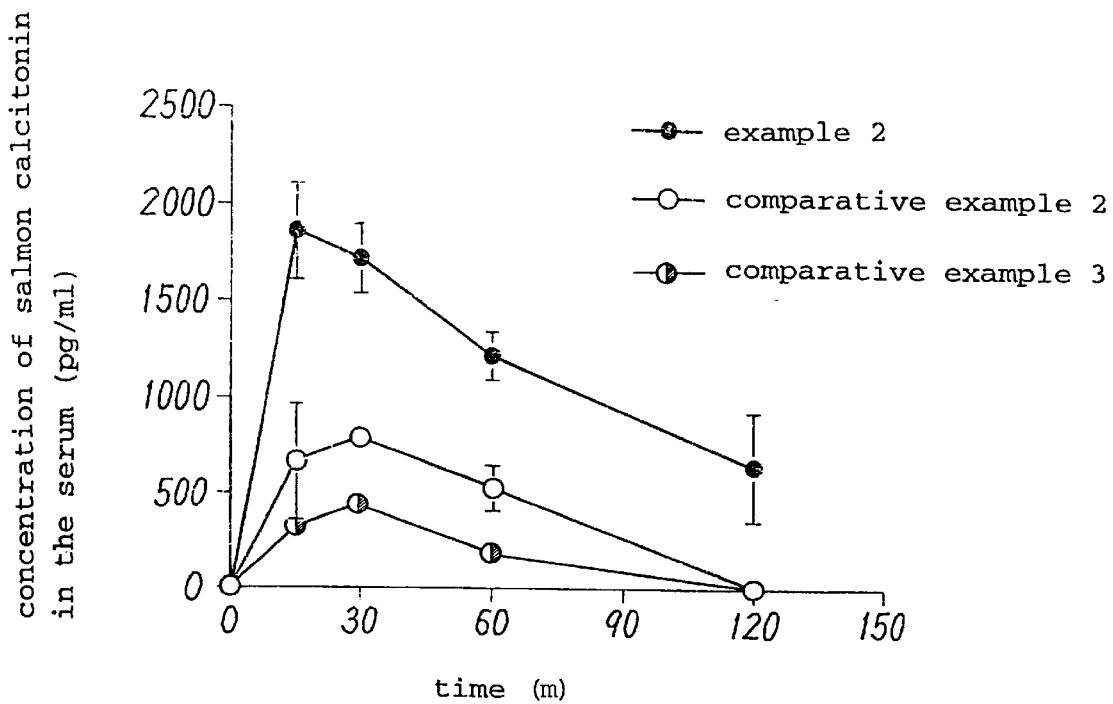
FIG. 9 is a view showing the change over time of the concentrations of salmon calcitonin in the serums of dogs, as observed by the donor devices in accordance with a second example, and second and third comparative examples.

FIG. 9 shows changes over time of the concentrations of salmon calcitonin in the serums in the event that the donor devices in the second example 2 and the second, third comparative examples were in use.

It is apparent from this drawing that if the donor device as per the second example was used, the salmon calcitonin having the maximum concentration of 1858±247 pg/ml (average±standard error) was detected after about 15 minutes, while in the case of the second comparative example in which a layer having a physiologic saline was interposed between the silver electrode and the ion exchange layer, the maximum value of salmon calcitonin concentration was 803±75 pg/ml, and as compared with the second example, the difference was as low as 40%. With the donor device as per the second comparative example, the salmon calcitonin concentration after 120 minutes was found equal to zero, which shows that no drug is being absorbed at this point.

On the other hand, as compared with the result obtained from the test made by the use of the donor device free from the ion exchange layer as per the third comparative example, the maximum concentration of salmon calcitonin obtained by the use of the donor device as the second example was found to be about 4.5 times. The third comparative example also showed that the salmon calcitonin concentration had been reduced to zero after a lapse of 120 minutes with the drug remaining unabsorbed, whereas in the case of the donor device as per the second example, a high concentration was found to be retained for a long period of time.

TEST EXAMPLE 2

With reference to the donor device for use with the iontophoresis system in accordance with the present invention, the influence of the distance between the ion exchange layer and the unpolarizable electrode on the electric conductivity of the purified water has been studied as under-mentioned.

Figure 10:
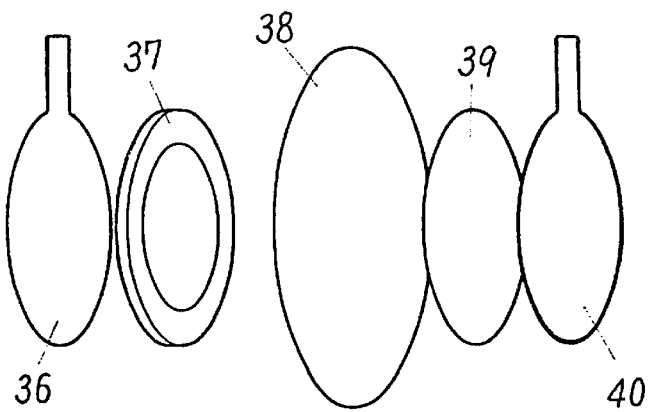
FIG. 10(a) is an exploded perspective view showing main parts of a test device as used in a second test example.
FIG. 10(b) is a sectional view showing main components of a test device as used in a second test example.
Figure 10:
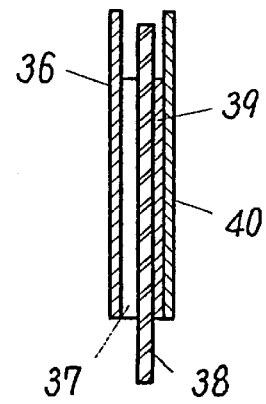

FIG. 10(*a*) is a exploded perspective view showing separated components of a test device used in the second test, and FIG. 10(*b*) is a sectional view showing the sections of the main components of the test used in the second test.

In the both drawings, 36 designates a silver electrode, 37 an O-ring, 38 an ion exchange membrane, 39 an electrolyte contained layer, and 40 a silver chloride electrode.

As illustrated in FIG. 10(*a*), the test device used in this test comprises silver electrode 36 having an area of 3.14 cm$^2$, O-ring 37, ion exchange membrane (A-201, Asahi Kasei) 38, electrolyte contained layer 39 made of sodium chloride contained polyvinyl alcohol gel, and silver chloride electrode 40. The silver electrode 36 is corresponding to the unpolarizable electrode of the donor device, ion exchange membrane 38 to the ion exchange layer, and electrolyte contained layer 39 to the drug holding layer respectively.

A test device as shown by FIG. 10(b) was prepared as provided with O-ring 37 incorporating a purified water itself or a purified water holder member impregnated with purified water, wherein the silver electrode 36 acts as an anode, and the silver chloride electrode 40 as a cathode. 1V of constant voltage was applied by a DC power source to the test device so as to determine the current value passing between the silver electrode 36 and silver chloride electrode 40. This measurement was carried out using O-rings 37 having different thickness of from 0.5 to 5 mm, and different thickness of purified water or separate purified water holding members impregnated with purified water. The result will be described with reference to FIG. 11.

Figure 11:
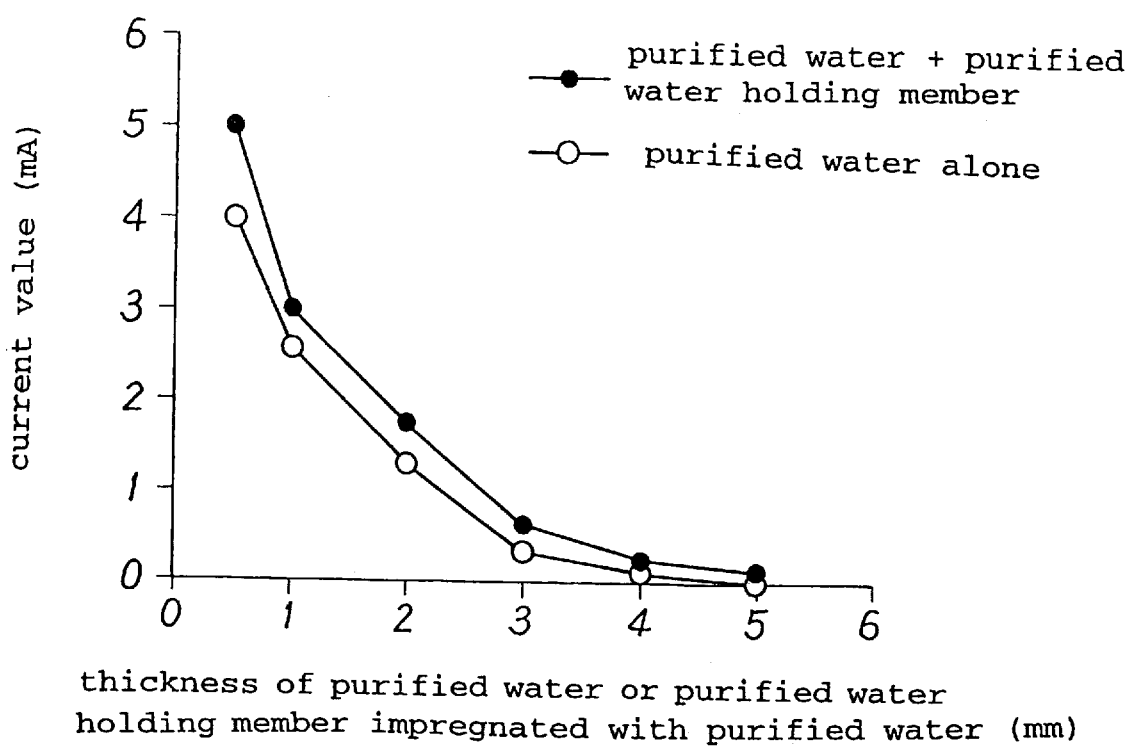
FIG. 11 is a view showing the relation between the thickness of purified water or a purified water holding member impregnated with purified water and the current value.
Figure 12:
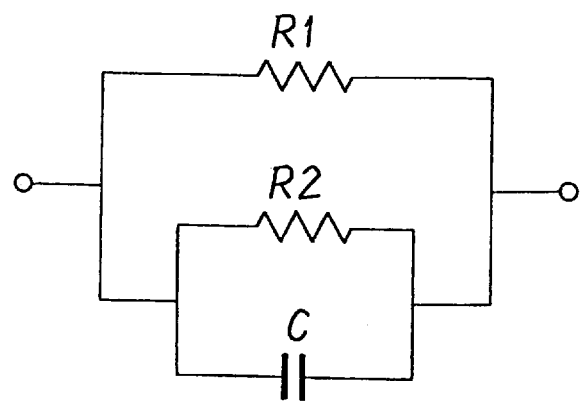
FIG. 12 shows an equivalent circuit for identifying the skin electrically.
Figure 13:
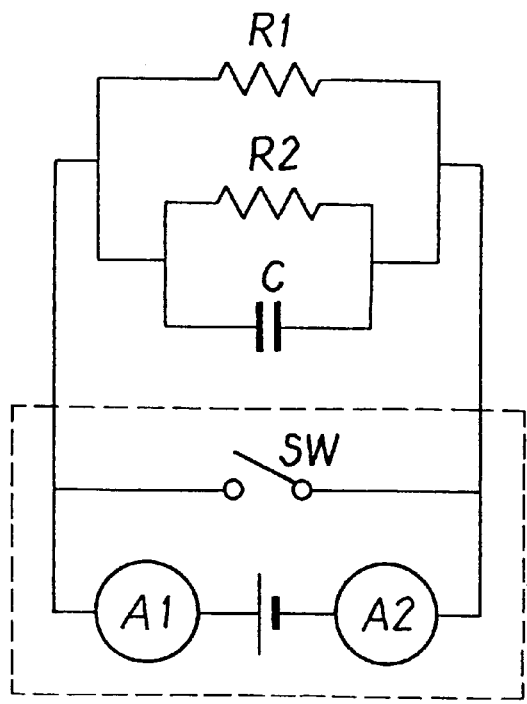
FIG. 13 is a typical view showing the measurement for current detection by a conventional constant current controllable pulse depolarization-type iontophoresis system.
Figure 14:
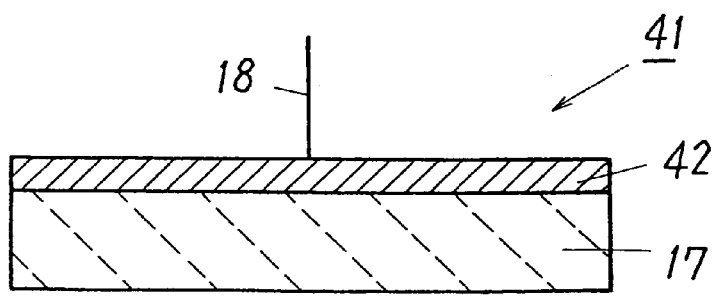
FIG. 14 is a sectional view showing main components of a conventional donor device.

FIG. 11 is a view showing the relation between the thickness of purified water or purified water holding member impregnated with purified water and the current value.

It is apparent from this drawing that if the thickness of purified water or purified water holding member impregnated with purified water is increased from 0.5 mm to 5 mm, the current value represented a rapid drop from 5 mA down to 0 mA. The provision of a purified water holding member impregnated with purified water showed an increase of the current value by about 20% in comparison with the case that the purified water was contained in the O-ring instead.

The above result has made it clear that the thickness of the purified water layer, which is disposed between the non-polarity electrode and the ion-exchange layer, in the donor device, is 0.01 to 4 mm, preferably 0.01 to 3 mm, and more preferably 0.01 to 2 mm. Moreover, the result adds that the employment of a purified water layer constituted by a purified water holding member impregnated with purified water may contribute to further improvement of the electric conductivity in the purified water layer rather than use a purified water alone.

INDUSTRIAL AVAILABILITY

As discussed earlier, the following outstanding effects may be obtained from the iontophoresis system of the present invention.

In accordance with the iontophoresis system of the present invention, the current value substantially involved in the delivery of drug to the skin or mucosal membrane may be grasped with an extreme precision as an effective current value, variation in the drug delivery quantity due to the individual difference of the impedance of skin and mucosal membrane can be decreased by varying the pulse voltage/current applied between the donor and reference devices by the feedback control to put this effective current value under control for smooth delivery of a given quantity of drug into the living body so that a predetermined quantity of drug may be securely regulated for safe and effective administration of physiological activated substances with the result that an iontophoresis that is excellent in medicinal effect can be performed.

The precise grasping of the drug delivery quantity can afford a safe and reliable administration of a drug having its therapeutic range and toxic range of the concentration thereof in blood standing close to each other (a narrow therapeutic window).

Since the device has a very simple circuit arrangement and can be made small in size, it may provide an excellent iontophoresis in productivity, transferability, and versatility in installment location.

This particular iontophoresis system also serves as a pulse depolarization-type system wherein the local variation in the amplitude of pulse voltage is small, and electric stimulus to the skin or mucosal membrane can be reduced markedly, so that the skin may be protected against any possible injury including chemical burns or electrical burns resulting from the use of a higher electric current.

Referring to the donor device, ions eluted from the unpolarizable electrode can be separated from the drug holding layer by the ion exchange layer in the voltage application so as to prevent any obstruction by said ions to the drug movement or absorption of drug into the human body, thus to increase the transport number of drug and improve the absorption efficiency of drug to the skin or mucosal membrane.

The existence of only a trace of electrolyte within the purified water layer of the donor device may avoid any dispersion of the electrolyte to the drug holding layer to ensure that the medicinal efficiency will be improved without any obstacle to the drug movement.

Small voltage drop due to the use of the unpolarizable electrode in the donor device makes it possible to employ more portions of an applied voltage, which are contributable to the drug motion to ensure that the delivery efficiency for drug and energy efficiency as well will be improved by a small applied voltage.

Improving of the mechanical strength of the purified water layer in the donor device, holding of a space between the unpolarizable electrode and ion exchange layer, and spreading of the contact area may cause the purified water layer, unpolarizable electrode, and ion exchange layer to be strongly joined and the electric conductivity of the purified water layer to be improved, so that the absorption efficiency of drug into the body and the absorption quantity will be improved, and that the absorption of drug may be carried out for a long period of time with only a few deterioration over time involved.

There is a few variation of pH in the drug holding layer of the donor device, and the deterioration of drug hardly happens such that a stable medicinal effect may reliably be maintained and stimulus to the skin may be decreased.

In accordance with the control process for current of the iontophoresis system of the present invention, a correct grasping of the drug delivery quantity and a control process for current very useful for improvement of the medicinal effect can be obtained.

What is claimed is:

1. An iontophoresis system serving as a pulse depolarization-type iontophoresis system which includes a donor device and a reference device so as to apply pulse voltage/current into the living body interposed between said donor and reference devices, characterized in that it comprises a current detection unit for measuring as an effective current value the difference between the value of an applied current passing between said donor device and said reference device during application of pulse voltage/current and the value of a discharged current whose electric charge which said living body has been equipped with is released by a short-circuit formed between said donor device and said reference device when said application of pulse voltage/current is suspended, and a feedback control unit of making the amplitude of said pulse voltage/current variable to control said effective current value.

2. An iontophoresis system as defined in claim 1, characterized in that said current detection unit converts said effective current value to an effective voltage value, and said feedback control unit exerts feedback control on said amplitude of pulse voltage/current depending on said effective voltage value.

3. An iontophoresis system as defined in claim 2, characterized in that said current detection unit is provided with a smoothing resistance of smoothing said effective voltage value which is a conversion from said effective current value into a substantially constant value.

4. An iontophoresis system as defined in any of claims 1 to 3, characterized in that said feedback control unit provides control to make variable the pulse cycle or pulse duty ratio of said pulse voltage/current.

5. An iontophoresis system as defined in any of claims 1 to 4, characterized in that it has a depolarization circuit member disposed between said donor device and said reference device for short-circuiting said donor device and said reference device through a resistance when application of said pulse voltage/current is suspended.

6. An iontophoresis system as defined in any of claims 1 to 5, characterized in that said donor device comprises an unpolarizable electrode, an ion exchange layer, and a purified water layer containing a purified water and placed between said unpolarizable electrode and said ion exchange layer.

7. An iontophoresis system as defined in claim 6, characterized in that said purified water layer includes a purified water holding member impregnated with purified water.

8. An iontophoresis system as defined in claim 6 or 7, characterized in that said purified water layer is formed with a thickness of 0.01 to 4 mm.

9. An iontophoresis system as defined in any of claims 6 to 8, characterized in that said purified water has an electric conductivity of 0.01 to 1500 $\mu\Omega^{-1} \cdot cm^{-1}$.

10. A control process for current of the iontophoresis system serving as a control process for current of a pulse depolarization-type iontophoresis system including a donor device and a reference device and adapted to apply a pulse voltage/current into the living body interposed between said donor device and said reference device, characterized in that it comprises an effective current measurement step of measuring as an effective current value the difference between the value of an applied current passing between said donor device and said reference device during application of said pulse voltage/current and the value of a discharged current whose electric charge which said living body has been equipped with is discharged by a short-circuit formed between said donor device and said reference device when said application of pulse voltage/current is suspended, and a feedback control step of making the amplitude of said pulse voltage/current variable to control said effective current value.

* * * * *